July 14, 1964 J. R. TEMPLE Plant Pat. 2,423
LANTANA PLANT
Filed Sept. 16, 1963
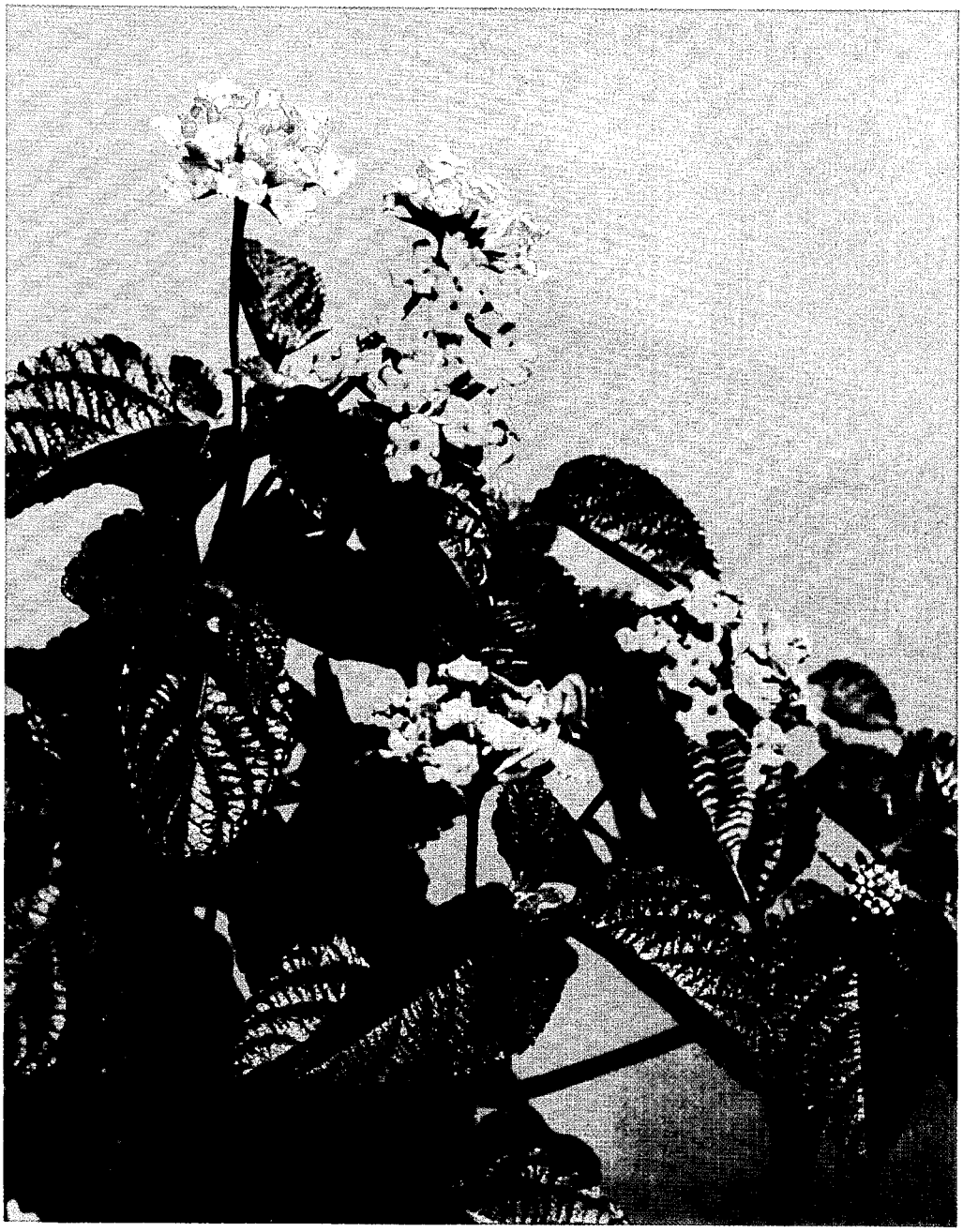
INVENTOR
John R. Temple
Webster & Webster
ATTYS.

United States Patent Office

Plant Pat. 2,423
Patented July 14, 1964

2,423
LANTANA PLANT

John R. Temple, Williams, Calif., assignor to Oki Nursery, Inc., Sacramento, Calif., a corporation of California Filed Sept. 16, 1963, Ser. No. 309,365
1 Claim. (Cl. Plt.—54)

This invention relates to a new and distinct variety of Lantana plant particularly characterized, as to novelty, by its compact habit of growth and attractive color of the flowers; all as hereinafter described in more detail.

The present variety of Lantana plant was originated by me in my garden at Williams, county of Colusa, State of California, as a seedling which resulted from a cross between the *Lantana camara* "Christine" as the seed parent and the *Lantana camara* "Radiation" as the pollen parent; both such parent varieties being unpatented.

Subsequent to origination by me of the instant variety of Lantana plant, it was asexually reproduced, on my behalf, by a commercial nursery located at Sacramento, county of Sacramento, State of California; such reproduction having been accomplished by cuttings from the original plant. Such cuttings, when they grew to the stage of full leaf and bloom, were found—in comparison to the original plant—to run true thereto in all respects.

The variety distinguishes itself from the parents, *Lantana camara* "Christine" and "Radiation," in the following respects:

The plant is slower growing, has shorter internodes, is substantially more compact in growth, and the leaves are of heavier and thicker texture.

The predominately Magenta Rose flowers, each of which is made up of a group of small individual florets arranged in a head, have more of an intense red tint than *Lantana camara* "Christine" and less orange tint than the *Lantana camara* "Radiation."

The drawing is an illustration, by photographic reproduction in color, of a portion of the plant and showing the leaves and flowers.

Referring now more specifically to the botanical details of this new and distinct variety of Lantana plant, the following is an outline description thereof; all major color plate identifications, by comparison with fresh specimens, being by reference to The British Colour Council Horticultural Colour Chart.

Class: *Lantana camara.*

Plant:

*Nature and growth.*—Upright bush form; much branched; slow growth; compact. Maximum height—3 feet. Maximum spread—4 feet.

*Stems.*—Succulent when new. Become woody, stiff, and brittle at maturity. Stout; hold plant upright.

*Foilage.*—Persistence—good. Density—moderately dense. Leaves: Size—average length, 2½"–2⅞"; average width, 1½"–1¾". Shape—ovate; margin serrate; apex acute to obtuse. Arrangement—opposite; petiole averages ½" to ¾" in length. Color—topside, Parsley Green (oo962); underside, Willow Green (ooo862/1). Appearance and texture—very creased; thick and crisp; moderately pubescent; ribs prominent on underside; moderately glossy on topside but less on underside. Aroma of leaves—resembles oil of eucalyptus.

*Blooming habit.*—Blooms profusely.

Flowers:

*Arrangement.*—Florets clustered in a hemispherical head 1¼" to 1¾" in diameter. Average 20 to 27 florets per head. Strong peduncle which averages 1½" to 2" in length, and is slightly pubescent. Heads borne mainly on terminal growth.

*Florets.*—Individually quite small. Average ½" to ⅝" in length. Average ⅜" to 7/16" in width.

*Color.*—Florets of a cluster are usually Magenta Rose (o27) to Magenta (27). In some clusters, however, certain of the florets are Lemon Yellow (4/1), with the remainder varying in shade between yellow and Magenta, such as Marigold Orange (11/2).

*Discoloration.*—Turn dark with age. Nearly black when wither and drop.

*Aroma.*—Slightly resembles citrus.

The herein described Lantana plant, including the foliage and flowers, may vary in slight detail due to climatic and soil conditions under which the variety may be grown; the present description being of the variety as grown in the Sacramento Valley of California.

The following is claimed:

A new and distinct variety of Lantana plant of upright, much branched, bush form, substantially as illustrated and described, characterized—as to novelty and in comparison with the parent varieties "Christine" and "Radiation"—by slower and more compact growth, shorter internodes, heavier and thicker textured leaves, and flowers which have more of an intense red tint than the "Christine" and less orange tint than the "Radiation"; the flowers usually being Magenta Rose to Magenta in the entirety, but in some instances are yellow in part with the remainder shading between yellow and Magenta.

No references cited.